United States Patent [19]

Sharif

[11] Patent Number: 5,217,632

[45] Date of Patent: Jun. 8, 1993

[54] PROCESS FOR PREPARATION AND COMPOSITION OF STABLE AQUEOUS SOLUTIONS OF BORON ZIRCONIUM CHELATES FOR HIGH TEMPERATURE FRAC FLUIDS

[75] Inventor: Sharif Sharif, Midland, Tex.

[73] Assignee: Zirconium Technology Corporation, Midland, Tex.

[21] Appl. No.: 880,650

[22] Filed: May 11, 1992

[51] Int. Cl.$^5$ .............................................. E21B 43/26
[52] U.S. Cl. .............................. 252/8.551; 252/315.3
[58] Field of Search ............... 556/7; 252/8.551, 315.3

[56] References Cited

U.S. PATENT DOCUMENTS

| | | | |
|---|---|---|---|
| 3,651,794 | 10/1971 | Nimerick | 252/8.551 X |
| 3,766,984 | 10/1973 | Nimerick | 166/294 |
| 3,794,115 | 2/1974 | Skagerberg | 166/294 |
| 3,856,541 | 12/1974 | Martin | 166/294 X |
| 3,974,077 | 8/1976 | Free | 252/8.551 |
| 4,021,355 | 5/1977 | Holtmyer et al. | 252/8.551 |
| 4,033,415 | 7/1977 | Holtmyer et al. | 252/8.551 X |
| 4,428,432 | 1/1984 | Pabley | 252/8.551 X |
| 4,463,810 | 8/1984 | Hill | 252/8.551 X |
| 4,514,309 | 4/1985 | Wadhwa | 252/8.551 |
| 4,543,131 | 9/1985 | Purinton, Jr. | 252/8.552 X |
| 4,553,601 | 11/1985 | Almond et al. | 252/8.551 X |
| 4,568,481 | 2/1986 | Harris, Jr. | 252/8.551 X |
| 4,619,776 | 10/1986 | Mondshine | 252/8.551 |
| 4,635,727 | 1/1987 | Anderson et al. | 252/8.551 X |
| 4,659,811 | 4/1987 | Wu | 252/8.551 X |
| 4,679,631 | 7/1987 | Dill et al. | 252/8.553 X |
| 4,767,550 | 8/1988 | Hanlon et al. | 252/8.551 |
| 4,780,223 | 10/1988 | Baranet et al. | 252/8.551 |
| 4,986,353 | 1/1991 | Clark et al. | 252/8.551 X |
| 4,986,354 | 1/1991 | Cantu et al. | 252/8.551 X |
| 5,007,481 | 4/1991 | Williams et al. | 252/8.551 X |
| 5,026,735 | 6/1991 | Stern | 252/315.3 X |
| 5,067,566 | 11/1991 | Dawson | 252/8.551 X |
| 5,095,987 | 3/1992 | Weaver et al. | 166/276 |
| 5,143,157 | 9/1992 | Harms | 252/8.551 X |
| 5,145,590 | 9/1992 | Dawson | 252/8.551 |
| 5,160,445 | 11/1992 | Sharif | 252/8.551 |
| 5,160,643 | 11/1992 | Dawson | 252/8.551 |

*Primary Examiner*—Gary L. Geist
*Attorney, Agent, or Firm*—Robert C. Peterson

[57] ABSTRACT

The present invention relates to a new process for preparing boron zirconium chelate solutions which are stable on the addition of acid bases, boiling, high dilution and/or aging. These chelates are useful in several industries, especially in the petroleum industry for frac fluids for treating oil or gas bearing strata especially deep hot wells. The boron zirconium chelates are prepared by forming a mixture of ammonium hydroxide, water soluble amines, sodium or potassium zirconium alpha hydroxy carboxylates selected from lactates, citrates, tartrates, glycolates, maliates, saccharates, gluconates, glycerates and mandelates, with polyols such as glycerin, erythritol, arabitol, xylitol, sorbitol, dulcitol, mannitol, inositol, monosaccharides and disaccharides and with water. This mixture is blended and then boric acid or borax as a source of boron is added and the pH is adjusted using inorganic or organic bases and/or inorganic carbonates and bicarbonates. The boron zirconium chelate solutions contain 0.1–3.0% by weight $ZrO_2$, 5–25% by weight polyols; 2–20% by weight of $B_2O_3$ with a weight ratio of $B_2O_3:ZrO_2$ between 5:1 and 20:1. The pH is maintained within the range 7.0–10.0.

28 Claims, 14 Drawing Sheets

PROCESS FOR PREPARATION AND COMPOSITION OF STABLE AQUEOUS SOLUTIONS OF BORON ZIRCONIUM CHELATES FOR HIGH TEMPERATURE FRAC FLUIDS

FIELD OF THE INVENTION

The invention relates to a novel process for the preparation of stable aqueous solutions of boron zirconium chelates at 100% chemical yield without effluent or solid waste. The novel boron zirconium chelate solutions are stable toward freeze and thaw cycles, the addition of acids, bases, boiling, dilution and aging.

BACKGROUND OF THE INVENTION

It is well known that boric acid is a very weak, inorganic acid and the borate ion does not exist as such until the pH is sufficiently high to react with more firmly bound second and third hydrogens. The borate ion complexes with many compounds, for example certain polysaccharides like guar and locust bean gum as well as polyvinyl alcohol. At a high pH above 8, the borate ion exists and is available to cross-link and cause gelling. At lower pH, the borate is tied up by hydrogen and is not available for cross-linking, thus gelation caused by borate ion is reversible.

According to Friedman, U.S. Pat. No. 3,800,872, if boric acid or borax is added to a 1% fully hydrated guar solution, the solution will gel. If, however, the procedure is reversed and one attempts to dissolve guar in a solution containing borax, hydration will not occur. The guar then appears to be water insoluble and no viscosity increases will be measured. The reason for this is that if the borate ion finds two or more guar molecules close together, there is a fair probability that it will link them together.

If, on the other hand, the borate gets to the slowly hydrating molecule before the guar molecules get close together to link, the intermolecular distances are too large to be spanned by the small borate ion. This causes the borate to use all its functional points to hook to one guar molecule shielding it from hydration. If a very dilute guar solution is allowed to fully hydrate and subsequently borated, the solution loses viscosity.

Another way in which borate ions form a complex is with a cis diol where two alcohol groups are on adjacent carbon atoms. If boric acid is added to a cis diol like glycerol, the resulting chelate holds the borate ion so tightly that the hydrogen becomes relatively labile. This makes a strong acid of boric acid. If a cis diol is added to a borate gel guar, the gel disappears because the diol attracts the borate more strongly then does the guar. Consequently, this aqueous gelling is a reversible process. Friedman goes on to discuss boric acid or borax as a cross-linker for aqueous flooding medium for an oil and gas reservoir.

Mondshine, U.S. Pat. No. 4,619,776, discloses that it is well known that organic polyhydroxy compounds having hydroxyl groups positioned in the cis-form on adjacent carbon atoms or on carbon atoms in a 1,3-relationship react with borates to form five or six member ring complexes. At alkaline pH's of above about 8, these complexes form didiols cross-link complexes. Mondshine goes on to state that such reversible reactions lead to a valuable reaction with disassociated borate ions in the presence of polymers with the required hydroxyl groups in a cis-relationship. The reaction is fully reversible with changes in pH. An aqueous solution of the polymer will gel in the presence of borate when the solution is made alkaline and will liquify again when the pH is lowered below about 8. If the dried powder polymer is added to an alkaline borate solution, it will not hydrate and thicken until the pH has dropped below about 8. The critical pH at which gelation occurs is modified by the concentration of dissolved salts. The effect of the dissolved salts is to change the pH at which a sufficient quantity of disassociated boric ions exist in solution to cause gelation. The addition of an alkali metal base such as sodium hydroxide enhances the effect of condensed borate such as borax by converting the borax to the disassociated metaborate.

Known polymers which contain an appreciable content of cishydroxyl groups are exemplified by guar gum, locust bean gum, dextrin, polyvinyl alcohol and derivatives of these polymers. Derivatives tend to react less with the borate ion as the amount of substituting group in the molecule increases. This results because of the sheer bulk of substituting groups changes the regular alternating and simple number branched linear configuration of the molecule and prevents adjacent chains from approaching as closely as before and a substitution of secondary cis-hydroxyl positions decreases the number of such unsubstituted positions available for complexing with the borate ion. As further pointed out by Mondshine, hydraulic fracturing is a widely used method for stimulating petroleum producing subterranean formations and is commonly performed by contacting the formation with a viscous fracturing fluid having particulated solids, widely known as propping agents, suspended therein applying sufficient pressure to the fracturing fluid to open a fracture in the subterranean formation and maintaining this pressure while injecting the fracturing fluid into the fracture at a sufficient rate to extend the fracture into the formation. When the pressure is reduced, the propping agents within the fracture prevent the complete closure of the fracture.

The properties that a fracturing fluid should possess are, among others, a low leak-off rate, the ability to carry a propping agent, low pumping friction loss and it should be easy to remove from the formation. Low leak-off rate is a property that permits the fluid to physically open the fracture and one that controls its areal extent. The ability of the fluid to suspend a propping agent is controlled by additions. Essentially, this property of the fluid is dependent upon the viscosity and density of the fluid and upon its velocity. Friction reducing additives are added to fracturing fluids to reduce pumping loss due to friction by suppression of turbulence in the fluid. To achieve maximum benefit from fracturing, the fracturing fluid must be removed from the formation. This is particularly true with the viscous fracturing fluids. Most such viscous fluids have built in breaker systems that reduce the viscosity gels to low viscosity solutions upon exposure to temperatures and pressures existing in the formation. When the viscosity is lowered, the fracturing fluid may readily be produced from the formation. Mondshine states that he has found that superior guar containing hydraulic fracturing fluids having enhanced thermal stability and decreased leak-off rate can be obtained utilizing ½ to 15 kilograms per cubic meter of sparingly soluble borate having a slow solubility rate to provide sufficient borate ions to cross-link the guar polymer, raise the pH, and provide a reserve of available borate ions to cross-link the polymer at high temperatures. Mondshine goes on to suggest that alkaline earth metal borates or alkali metal alkaline earth metal borates have unique solubility characteristics which enable them to be used in the control cross-linking of aqueous systems containing guar polymers. The rate of cross-linking can be controlled by suitable adjustment of one or more of the following variables: initial pH of the aqueous solutions system, relative concentration of one or more of the sparingly soluble borates, the temperature of the borates, temperature of the aqueous system and particle size of the borate. In the patent, the inventor further describes a series of sparingly soluble borates for use in fracturing fluids.

On occasion, it is desirous to temporarily seal or plug a permeable formation located in a subterranean oil and gas formation having a bore hole therein. This may be done for several purposes such as, for example, so that other less permeable zones can be treated in some manner, i.e. fractured, acidized, etc. Many methods and compositions have been employed for temporarily plugging or sealing the openings or passageways located in such formations. Nimerick, U.S. Pat. No. 3,766,984 discusses at length the use of gels such as cross-link polysaccharides, and Nimerick suggests the use of an aqueous slurring composition containing a portion of the constituents of a granulated composition comprised of a galactomannan gum which has been treated with hydrophobing agent to render the gum hydrophobic (less hydrophilic than normal) when disbursed in an aqueous solution having a pH of at least 7.5, a pH control agent and a water soluble organic polymer suspending agent. Optionally, a degrading agent for a hydrated form of the gum and/or a cross-linking agent for hydrated gum and/or hydration agents can be employed.

Skagerberg, U.S. Pat. No. 3,794,115 describes a relatively low concentration of polymer which can be pumped through the system without using excessive high pressure and goes on to list numerous polymers suitable for use in aqueous solutions for forming bore hole plugs and further suggests the use of borax glass as one of a number of cross-linking agents including antimony and chromic ions.

SUMMARY OF THE INVENTION

The present invention relates to a new process for preparing boron zirconium chelate solutions which are stable on the addition of acids, bases, on boiling, at high dilution and/or aging; and therefor are useful as a frac solution for treating underground oil or gas bearing strata.

The novel products have the potential to be used in the production of efficient crosslinked gels using water soluble polymers such as guar and guar derivatives such as hydroxypropylguar (HPG) and carboxymethylhydroxypropyl guar (CMHPG), and also derivatized cellulosics such as carboxymethylhydroxyethyl cellulose (CMHEC), and the like. In general, the invention can be utilized in conjunction with various water soluble polymers to produce stable gels which will be useful in enhancing the production of oil and/or gas. The high-temperature stable gels utilizing the invention will also be useful in improving the injectivity of water and/or $CO_2$ to enhance the recovery of hydrocarbons in shallow and deep wells. The invention can conceivably be used in formation consolidation type well completion where gravel packing fluids are used. The use of similar, but inferior, borate crosslinkers in these applications are well documented in the patent literature. The new disclosed borate crosslinkers will significantly promote greater conductivity to enhance hydrocarbon recovery at temperatures substantially higher than are now possible with present products.

DETAILED DESCRIPTION OF THE INVENTION

Figure 1:
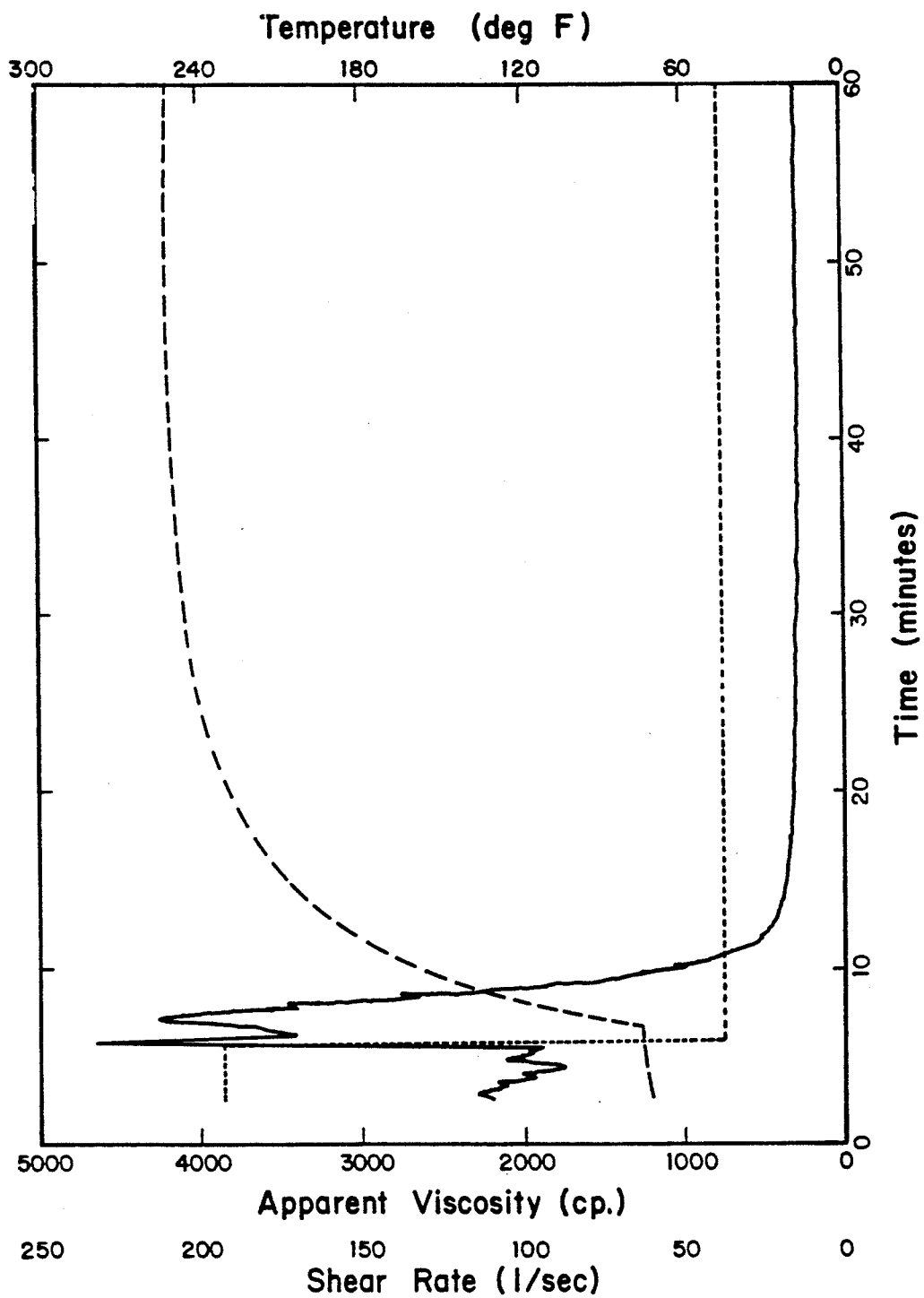
FIGS. 1–12 respectively represent graphs of the shear rate and apparent viscosity against time and temperature of the solutions of the present invention.

The novel boron zirconium chelates of the present invention may be prepared by forming a mixture of ammonia hydroxide, water soluble amines or amine derivatives, potassium or sodium zirconium alpha hydroxy carboxylates, a polyol such as glycerin, erythritol, arabitol, xylitol, sorbitol, dulcitol, mannitol, inositol, monosaccharides or disaccharides and water. The mixture is blended until it is relatively uniform then boric acid or borax as a source of boron is added to the mixture while stirring. Then an inorganic or organic base and/or inorganic carbonates and/or bicarbonates are used to adjust the pH of the final solution of boron zirconium chelate between 7 and 10. A sufficient quantity of the zirconium alpha hydroxy carboxylate and boron are used to provide a $ZrO_2$ content between 0.1 and 3.0%, a $B_2O_3$ to $ZrO_2$ weight ratio between 5:1 and 20:1 in the final solution, the $B_2O_3$ between 2 and 20% by weight in the final solution and polyols between 5–25% by weight in the final solution.

In one embodiment the process of preparing the boron zirconium chelate of the present invention utilizes solutions of sodium, potassium, ammonia hydroxide and/or amines zirconium lactate, citrate, tartrate and/or other zirconium alpha-hydroxy carboxylates, glycerin, other polyols and water.

The alkali metal ammonia and/or amines zirconium alpha-hydroxy carboxylates may be prepared in accordance with my prior invention described in my pending patent application Ser. No. 07/691,363, filed Apr. 25, 1991, entitled Process for Preparation of Stable Aqueous Solutions of Zirconium Chelates. Also, the aqueous solutions of zirconium chelates may be prepared as described by Van Meter in his U.S. Pat. No. 2,498,514. The boron zirconium chelates of the present invention involve the reaction between these zirconium alpha-hydroxy carboxylates and polyols in water with boric acid and/or borax then added and the pH adjusted with the aforesaid bases.

In a specific embodiment of the process, the quantities of glycerin, water and alkali metal zirconium chelate are mixed until a uniform blend is obtained. Then, boric acid or borax is added and the reaction batch is mixed for a period of about thirty minutes. Next, an alkali metal hydroxide is gradually added to the reaction batch while mixing.

Before the addition of alkali metal hydroxide, some of the boric acid may still be undissolved. When the addition of the alkali metal hydroxide is completed, a clear and stable solution product is obtained. The range of pH for boron zirconium chelate solution ranges from about 7 to about 10.0.

It should be noted that the claimed processes have 100% chemical yield and do not generate either organic and/or inorganic effluent and/or solid waste. The process utilizes only aqueous chemicals to produce purely aqueous products which eliminate the need for organic solvents and the attendant fire hazards and other disadvantages.

In this disclosure I claim a mixed B-Zr chelate complex which is water soluble with good stability on at least several freeze and thaw cycles, boiling, dilution and/or aging. In this solution product, I believe that the boron atoms are linked to the zirconium atoms through the lactate (or other alpha hydroxy carboxylate) groups and the glycerin (or other polyols) molecules. These two ligands are strong chelating agents and the produced B-chelate-Zr bonding cause the high stability of the product and it qualifies it as an efficient and versatile crosslinker in high temperature fracturing fluids and other potential applications in the oilwell industry.

In my experimentation, I have determined that for best results the boron zirconium chelate solution should have a weight ratio of between 5:1 to 20:1 of $B_2O_3$ to $ZrO_2$.

EXAMPLE 1

The following ingredients were utilized in the preparation of a laboratory sample of one of the disclosed novel products:
100 gm distilled $H_2O$
1040 gm of glycerin
300 gm of sodium zirconium lactate (7.0% $ZrO_2$)
380 gm of boric acid
277 gm of 50% sodium hydroxide The above quantities of glycerin, water and sodium-zirconium lactate were mixed until a uniform blend was obtained. Boric acid was added and the reaction batch was mixed for at least 30 minutes. The 277 gms of 50% sodium hydroxide were gradually added to the reaction batch while mixing.

Before the addition of the sodium hydroxide some of the boric acid was still undissolved. When the addition of the 50% NaOH was completed a clear and stable solution product was obtained. The pH of the product in several preparations ranged from 7.0 to 8.0. The ratio of $B_2O_3$ to $ZrO_2$ was 10 to 1 (by weight).

The reaction proceeds at room temperature but is exothermic upon addition of the sodium hydroxide.

EXAMPLE 2

Using the following ingredients, a similar product as the one obtained from Example 1 using the same method of preparation was obtained.
1040 gm of sorbitol
300 gm of sodium zirconium lactate (7.0% $ZrO_2$)
380 gm of boric acid
300 gm of 50% sodium hydroxide
100 gm of distilled water The pH of the product is in the range of 8.0–8.5. The ratio of $B_2O_3$ to $ZrO_2$ as 10 to 1 (by weight).

EXAMPLE 3

The following ingredients were utilized in the preparation of a similar product to the one obtained from Example 1, using the same method of preparation.
1367 gm of glycerin
406 gm of ammonium zirconium lactate (7.0% $ZrO_2$)
489 gm of boric acid
300 gm of 28% ammonium hydroxide solution
100 gm of distilled water
pH of the product 8.0–8.5. The ratio of $B_2O_3$ to $ZrO_2$ was 10 to 1 (by weight).

EXAMPLE 4

The following ingredients were utilized in the preparation of a similar product to the one obtained from Example 1 using the same method of preparation.
1040 gm of glycerin
300 gm of sodium zirconium citrate (7.0% $ZrO_2$)
380 gm of boric acid
300 gm of 50% sodium hydroxide
100 gm of distilled water
pH of the product 8.0–8.5.

EXAMPLE 5

A product with a pH of 9.0–9.5 with a $B_2O_3:ZrO_2$ weight ratio of 10:1 was obtained using the same procedure as in Example 1 and the following ingredients.
100 gm of distilled water
1040 gm of glycerin
300 gm of sodium zirconium lactate (7.0% $ZrO_2$)
380 gm of boric acid
349 gm of 50% NaOH

EXAMPLE 6

The following ingredients were utilized in the preparation of a similar product to the one obtained from Example 1 by following the same method of preparation.
840 gm of glycerin
600 gm of sodium zirconium lactate (7.0% $ZrO_2$)
380 gm of boric acid
309 gm of 50% sodium hydroxide The product obtained had a pH of 7.5–8.5 and a $B_2O_3:ZrO_2$ weight ratio of 5.0:1.0.

EXAMPLE 7

The following ingredients were utilized in the preparation of a similar product to the one obtained from Example 1 by following the same method of preparation.
1040 gm of glycerin
250 gm of DI water
150 gm of sodium zirconium lactate (7.0% $ZrO_2$)
380 gm of boric acid
277 gm of 50% sodium hydroxide The above quantities of glycerin, water and sodium-zirconium lactate were mixed until a uniform blend was obtained. Boric acid was added and the reaction batch was mixed for at least 30 minutes. 277 grams of 50% sodium hydroxide were gradually added to the reaction batch while mixing. A clear solution was obtained with a pH of 7.0–7.5 and a $B_2O_3:ZrO_2$ weight ratio of 20:1.

Substitutes for sodium hydroxide used in various Examples can be one or mixture of ammonium hydroxide one or mixture of water soluble organic amines such as triethanolamine, diethanolamine. Also, a mixture of sodium hydroxide and any of these inorganic and organic bases can be used to prepare similar novel products to the one produced in the Examples. Further inorganic carbonates can be used such as sodium carbonate, sodium bicarbonate, potassium carbonate, potassium bicarbonate, ammonium carbonate, ammonium bicarbonate, and other inorganic carbonate and bicarbonate.

As in the Examples, similar products can be prepared by substituting for sodium zirconium lactate (or other alkali metal zirconium chelate) one, or a mixture of the following water soluble zirconium chelates.

1 sodium zirconium citrate
2 sodium zirconium tartrate
3 sodium zirconium glycolate
4 sodium zirconium maleate
5 sodium zirconium saccharate
6 sodium zirconium gluconate
7 sodium zirconium glycerate
8 sodium zirconium mandelate
9 ammonium zirconium lactate
10 ammonium zirconium citrate
11 ammonium zirconium tartrate
12 ammonium zirconium glycolate
13 ammonium zirconium maleate
14 ammonium zirconium saccharate
15 ammonium zirconium gluconate
16 ammonium zirconium glycerate
17 ammonium zirconium mandelate
18 potassium zirconium lactate
19 potassium zirconium citrate
20 potassium zirconium tartrate
21 potassium zirconium glycolate
22 potassium zirconium maleate
23 potassium zirconium saccharate
24 potassium zirconium gluconate
25 potassium zirconium glycerate
26 potassium zirconium mandelate
27 amine zirconium lactate
28 amine zirconium citrate
29 amine zirconium tartrate
30 amine zirconium glycolate
31 amine zirconium maleate
32 amine zirconium saccharate
33 amine zirconium gluconate
34 amine zirconium glycerate
35 amine zirconium mandelate In the above product, the following polyols can be used instead of, or mixed with glycerin to prepare similar products.

erythritol
arabitol
xylitol
sorbitol
dulcitol
mannitol
inositol
monosaccharides
disaccharides The pH of any of the new products can vary between 7.0–10.0 with a preferred range of 7.0–9.0. This variable is dependent on the amount and/or the chemical nature of the inorganic and/or the organic base(s) and/or inorganic carbonates and/or bicarbonates used in the preparation. The efficiency of a certain product, and the consistency of its performance increases with its pH.

$B_2O_3$ concentration of the products may vary between 2.0 and 20.0% by weight, and the $ZrO_2$ concentration between 0.1–3.0% by weight. The $B_2O_3:ZrO_2$ weight ratio may vary between 5:1 and 20:1.

TESTING

Various of the boron zirconium chelate solutions were tested as crosslinkers by an outside consultant (S. A. Holditch and Associates, Inc. petroleum engineering consultants).

For testing purposes, 40 lbs per 1000 gal of water of hydroxypropylguar (HPG) solution was used. Rheological measurements were made using a Fann Model 50C Rotational Viscometer (Rheometer). Since we are testing Newtonian fluids, this rotational viscometer is suitable for our tests.

The HPG solution was crosslinked with various of the novel zirconium borate crosslinkers of the present invention.

The tests herein enumerated utilized the following process for preparing the samples:

KCl was dissolved in deionized water to prepare a 1% KCl solution. 40 lbs per 1000 gal (ppt) of HPG was added to the 1% KCl solution. The polymer was allowed to hydrate while mixing for 30 minutes with a pH of 5–7. Next, 8 ppt of soda ash or 1.2 gal per 1000 gal (gpt) of sodium hydroxide solution (10% NaOH) was added to raise the base gel pH (HPG solution) to between a pH of 9–10. Finally the boron zirconium chelate crosslinkers were added and mixed to uniformity. A sample was placed in the Fann cup and the various parameters were determined in accordance with the known procedures for this rotational viscometer. The details of the samples tested are set forth in Table I.

TABLE I

Figure 2:
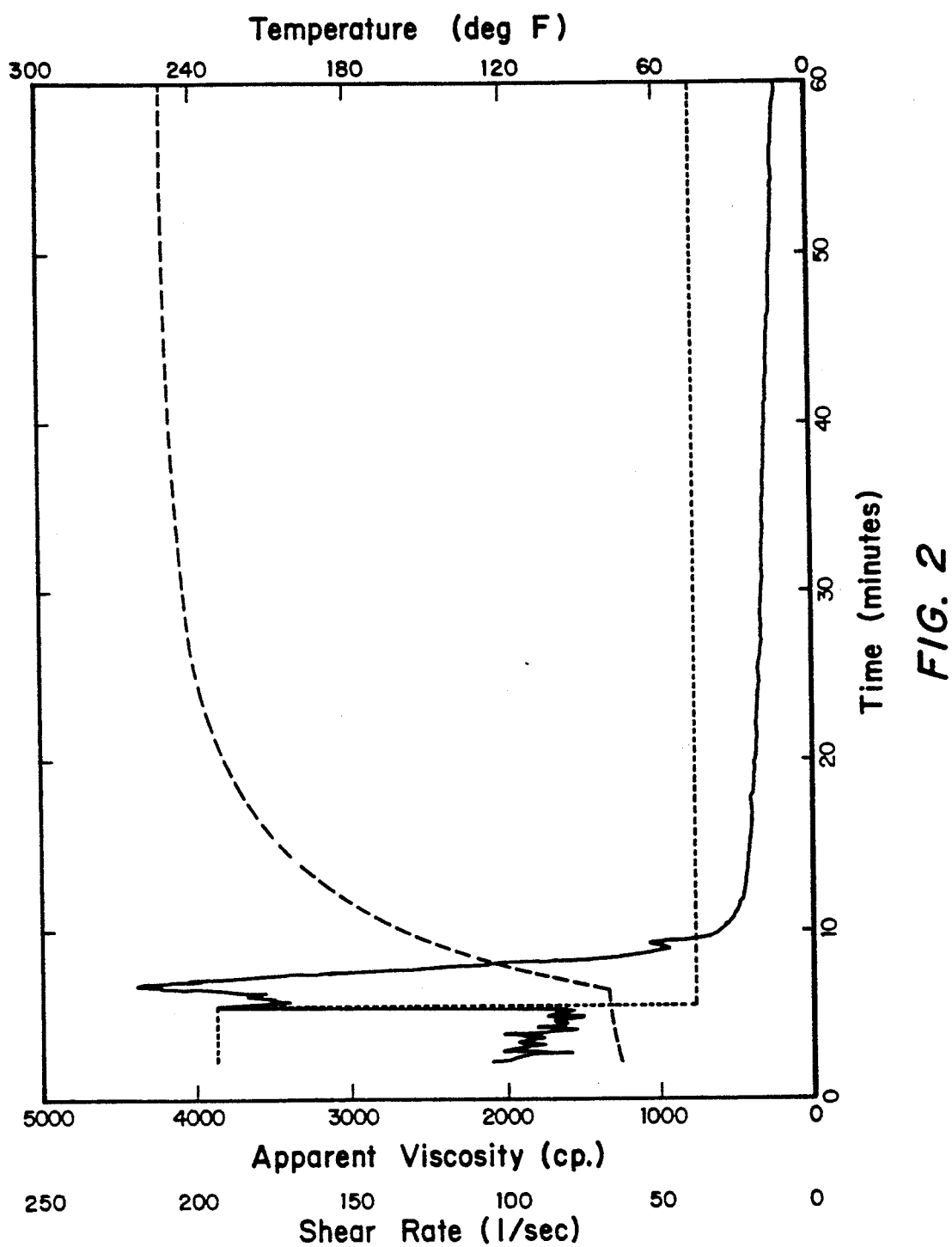
Figure 3:
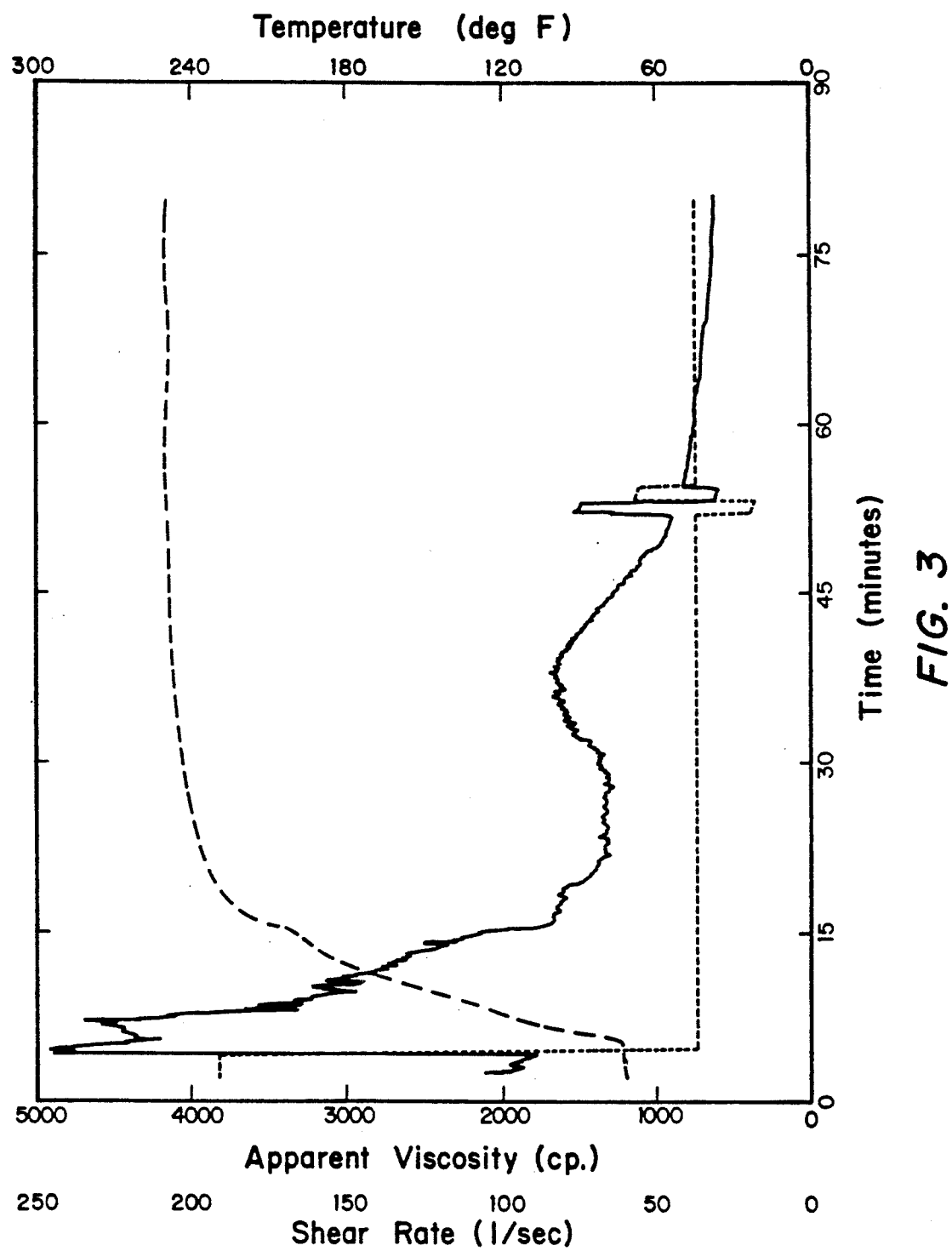
Figure 4:
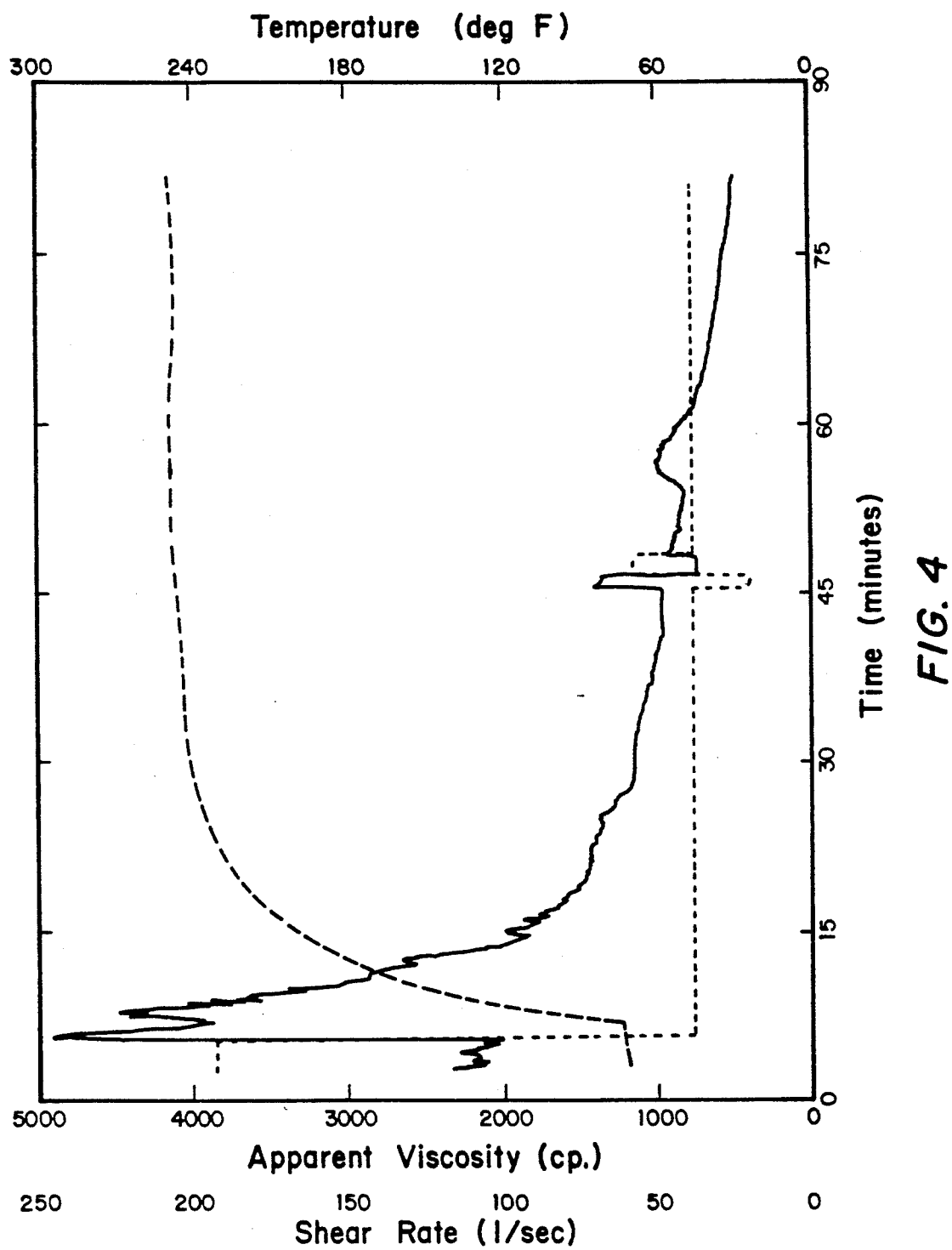
Figure 5:
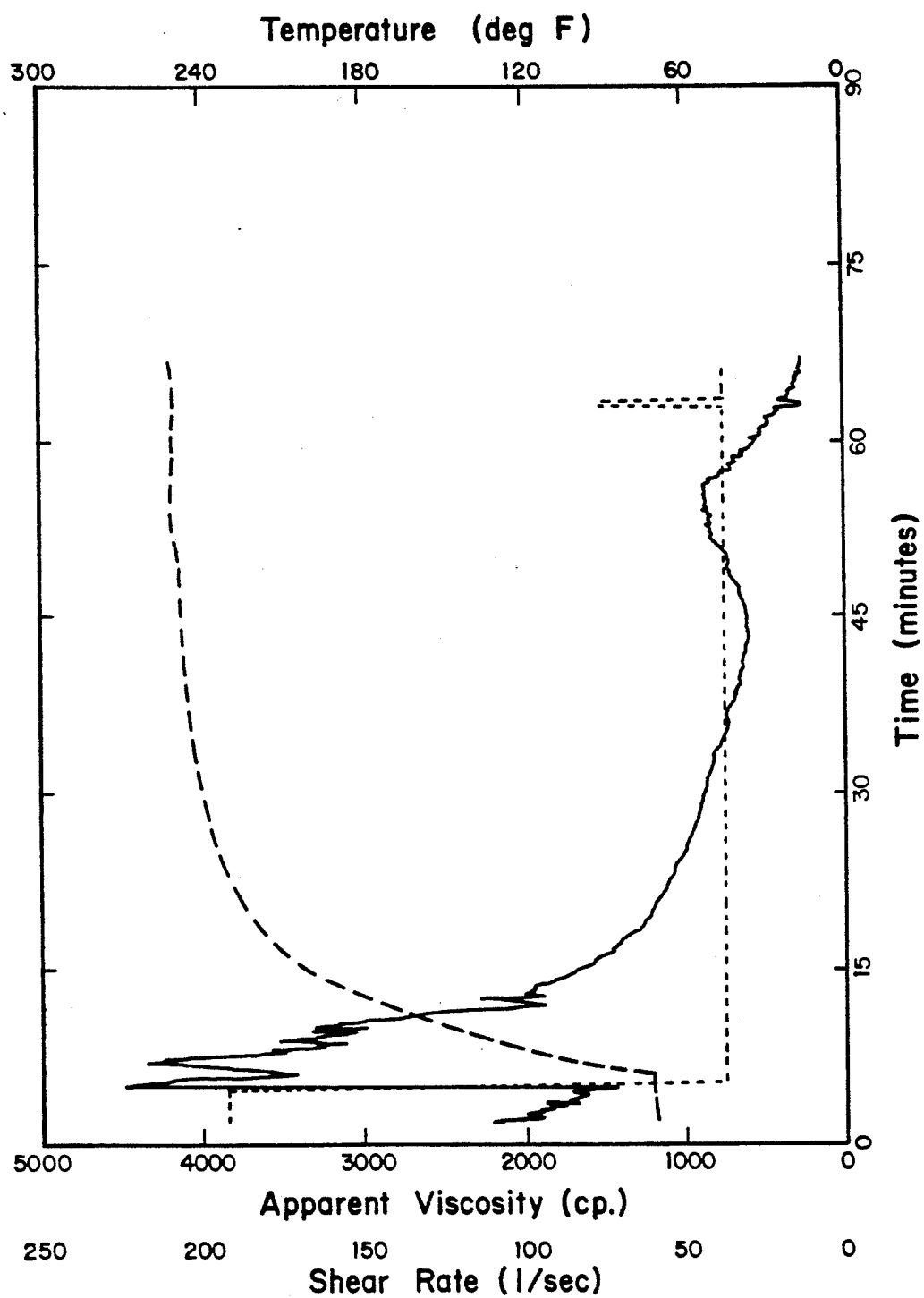
Figure 6:
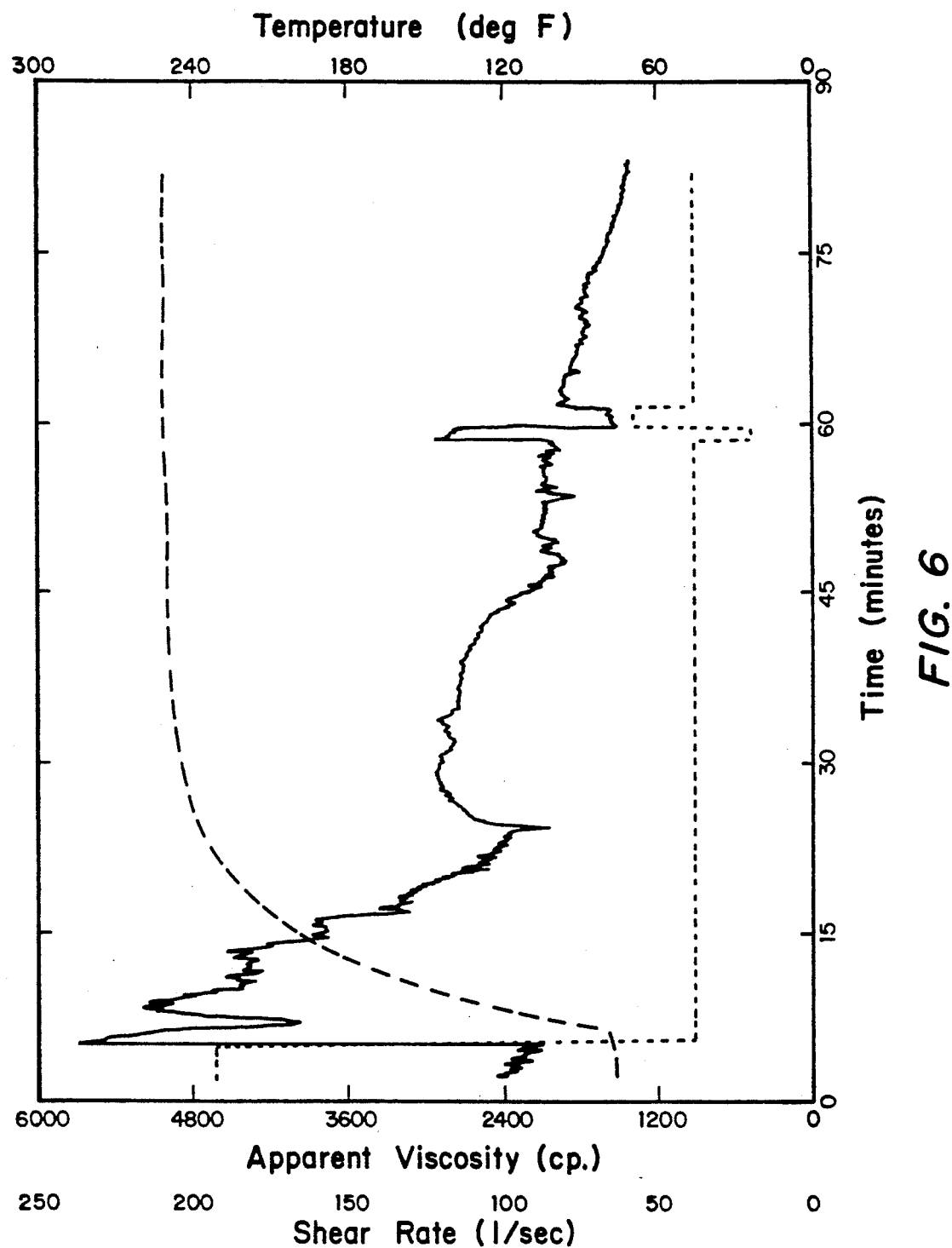

| TEST NO. | EXAMPLE NO. | $B_2O_3:ZrO_2$ WT. RATIO | SOLUTION/ HPG GPT | BUFFER TYPE | N' | K' | REMARKS OF TEST CONSULTANTS |
|---|---|---|---|---|---|---|---|
| 1 | | | 3.0 | Sodium hydroxide | | | In FIG. 1, there was a very rapid breakdown of the fluid as temperature increased. When the fluid was taken off the viscometer, there was some stringy crosslink present. |
| 2 | | | 4.0 | Sodium hydroxide | | | In FIG. 2, there was a very rapid breakdown of the fluid as temperature increased. When the fluid was taken off the viscometer, there was some stringy crosslink present. |
| 3 | 3 | 10:1 | 1.5 | Soda Ash | .2285 | .2994 | FIG. 3 shows the solution with over 1000 cp apparent viscosity after about 45 minutes. |
| 4 | 3 | 10:1 | 2.0 | Soda Ash | .4421 | .1467 | The performance in FIG. 4 would compare with such fluids as Versagel HT and YF-600 at comparable HPG loadings. |
| 5 | 1 | 10:1 | 1.5 | Sodium Hydroxide | .4865 | .2691 | In FIG. 5 the performance with the caustic soda was less than that with the soda ash simply from syneresis and slip. This reiterates the need for a buffer system with the borate gels or, for that matter, any other fracture fluid. |
| 6 | 1 | 10:1 | 1.5 | Soda Ash | .4865 | .2691 | Results in FIG.6 indicate this sample had a sustained viscosity in excess of 1000 cp for a period greater than one hour at test temperature of 250° F. The results are very favorable from the standpoint of representative fluids. There |

TABLE I-continued

Figure 7:
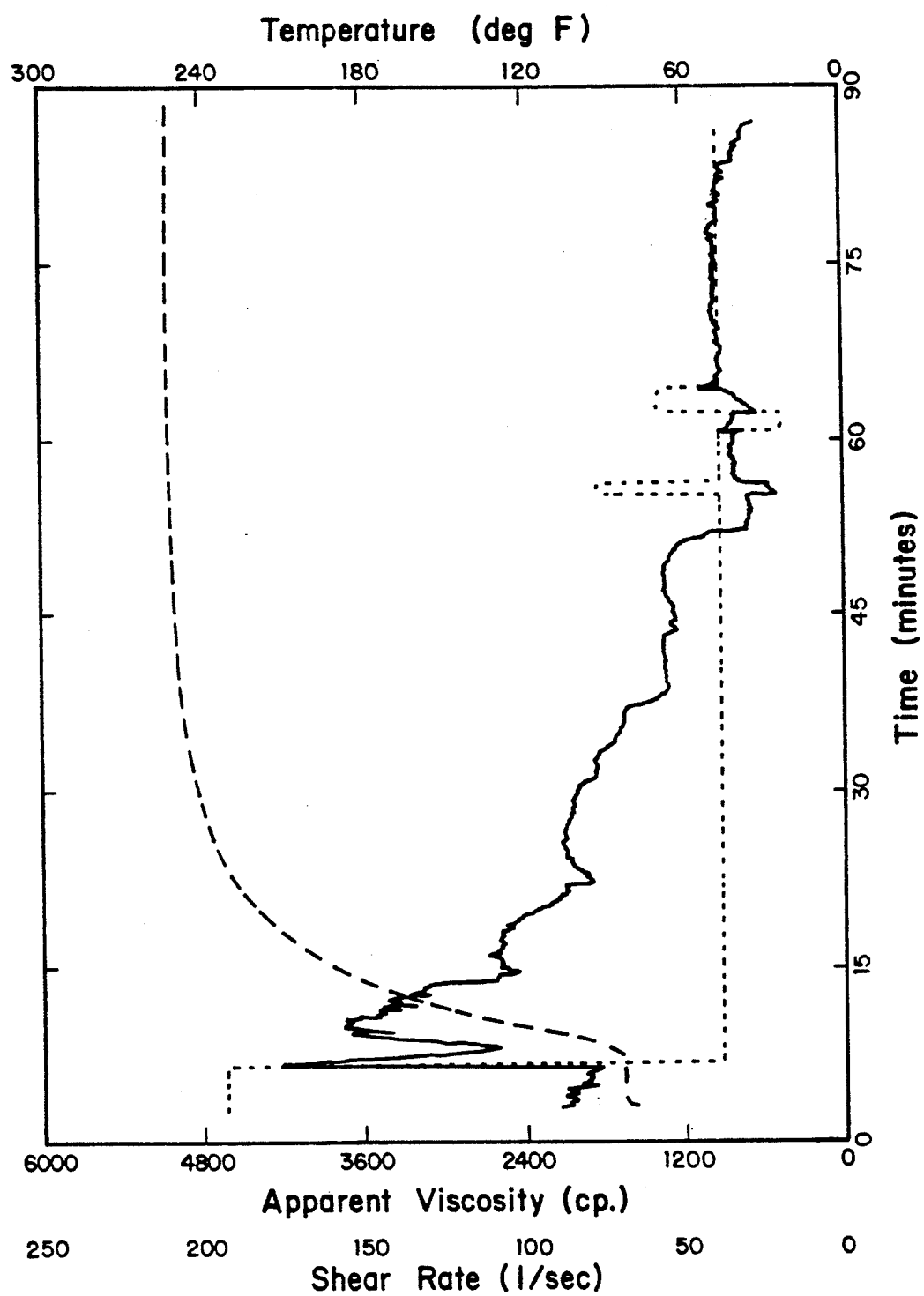
Figure 8:
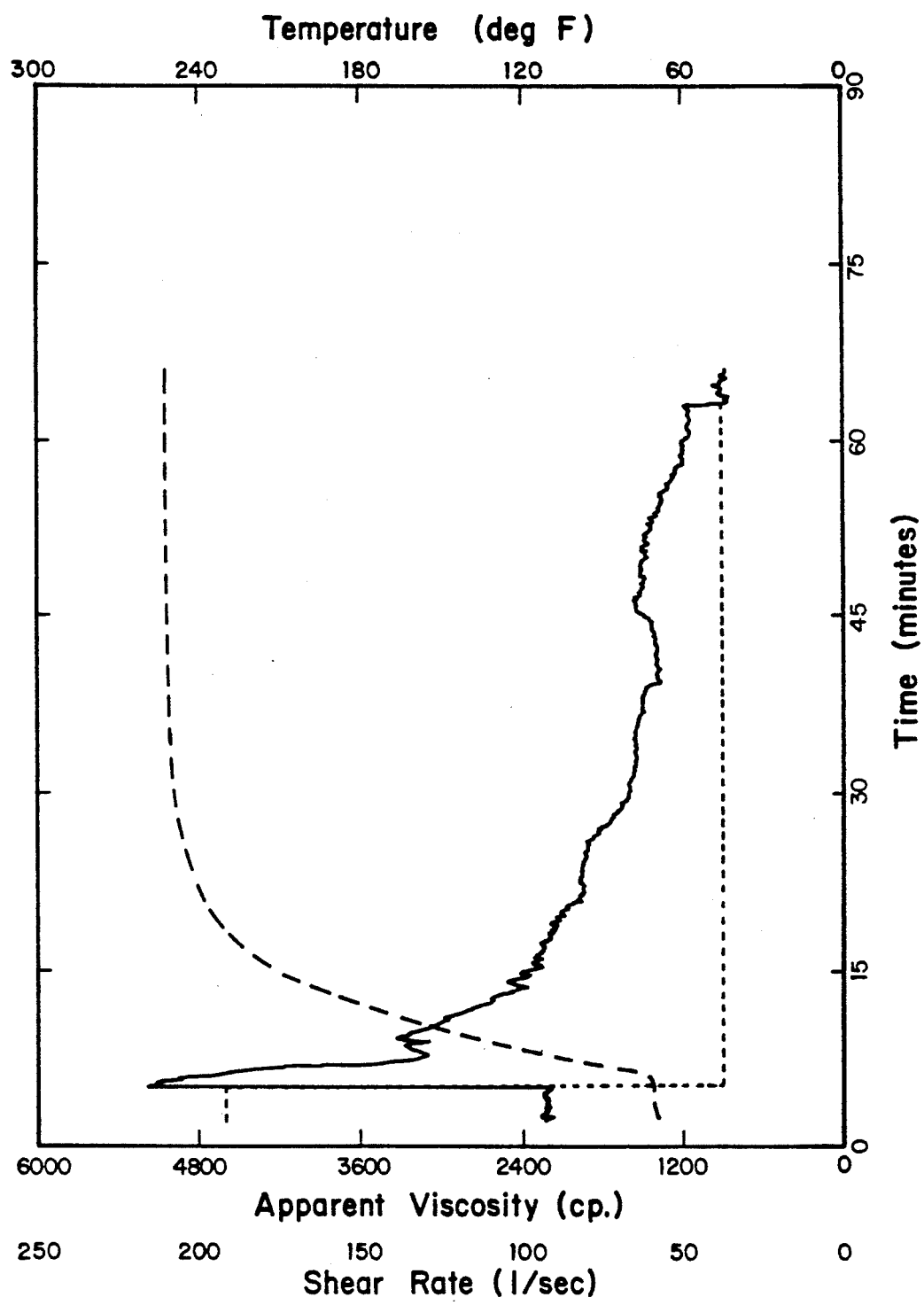
Figure 9:
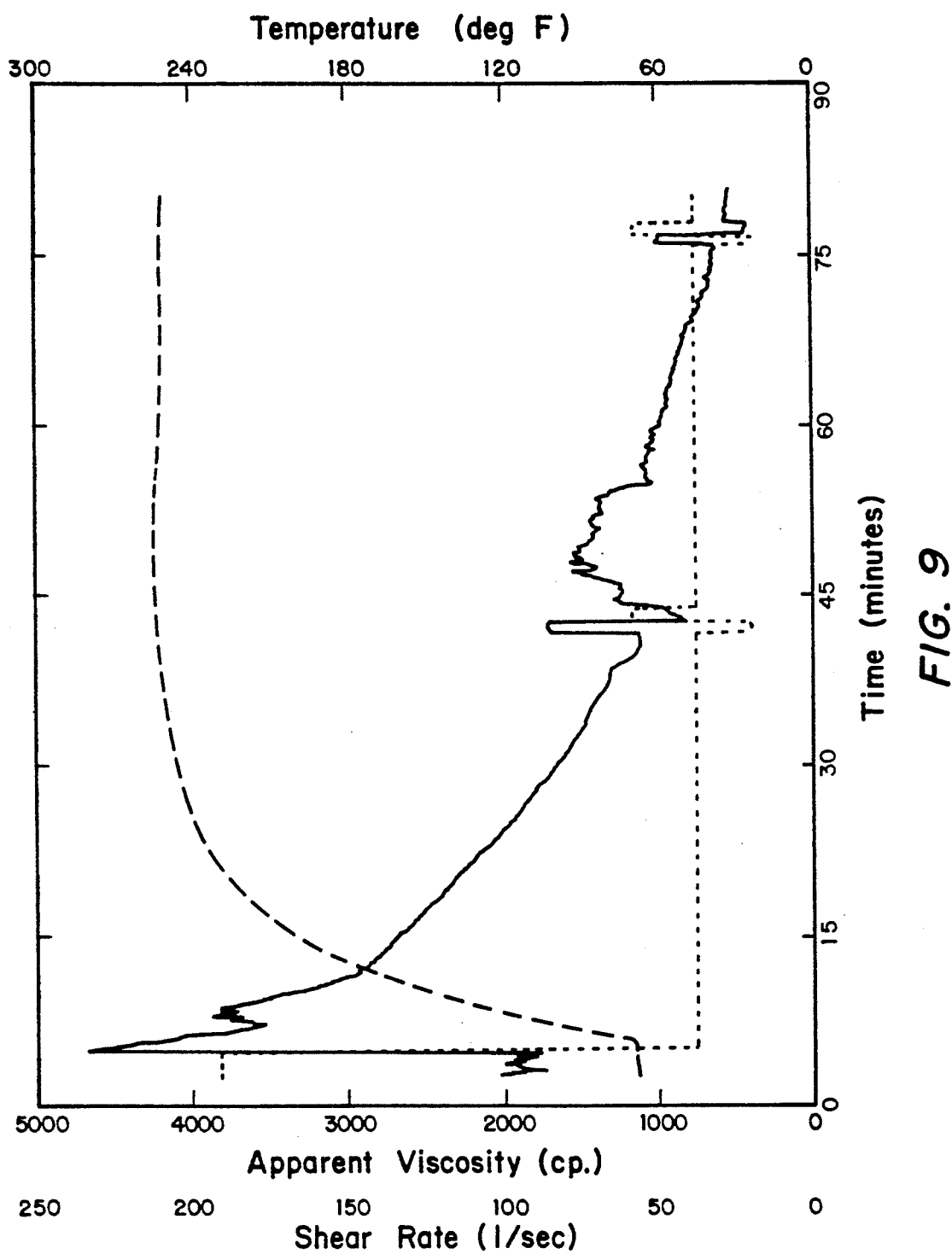
Figure 10:
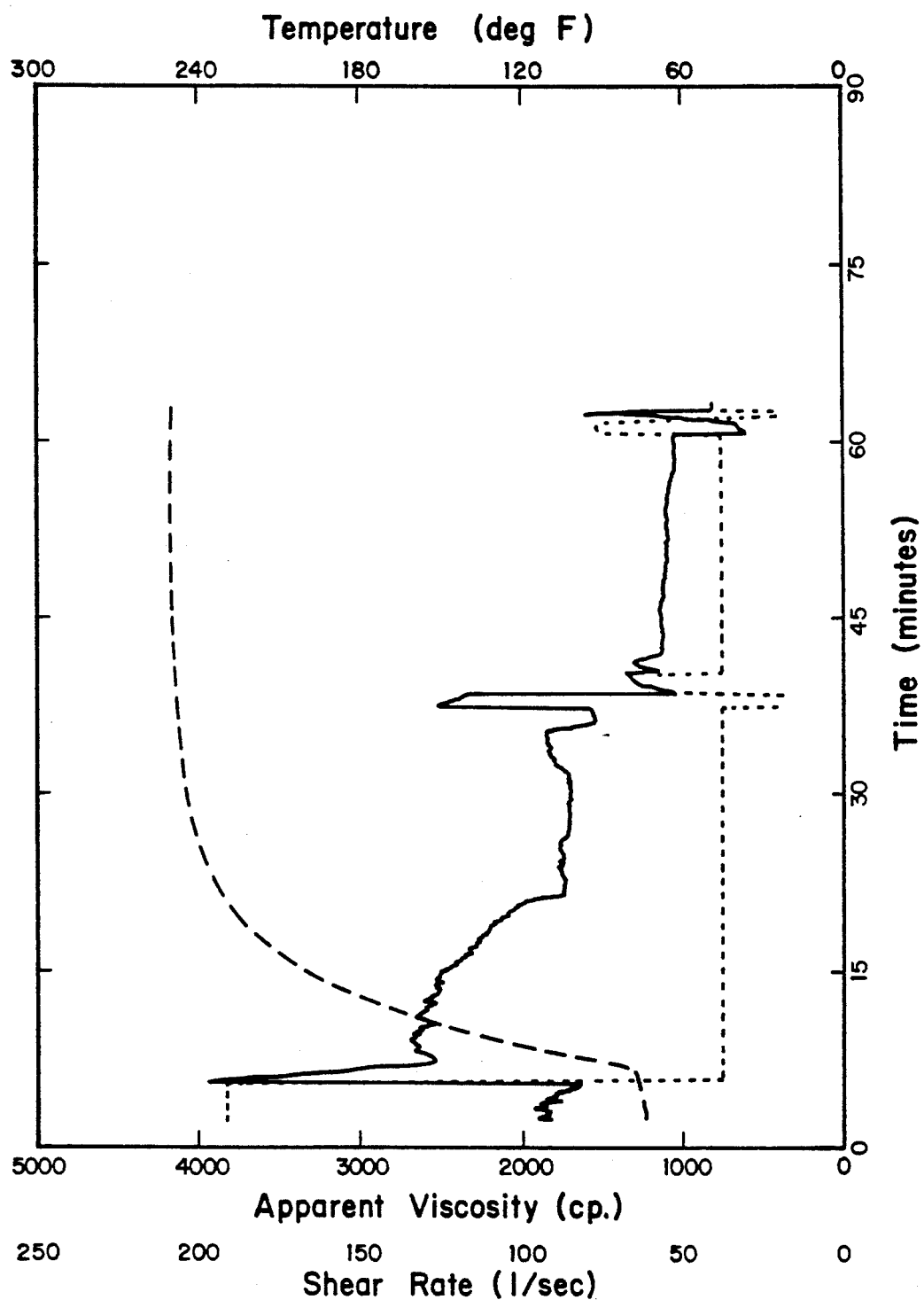
Figure 11:
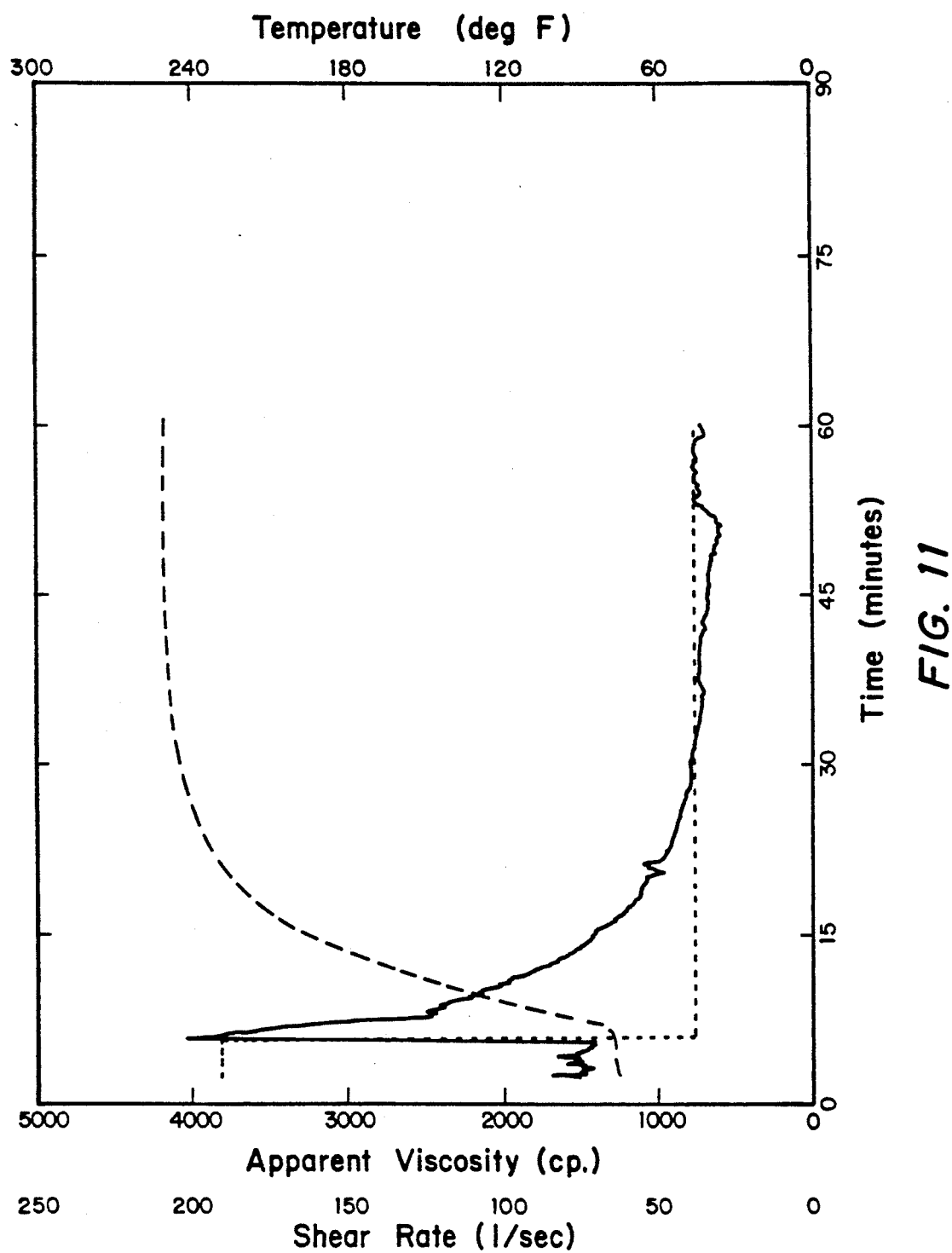
Figure 12:
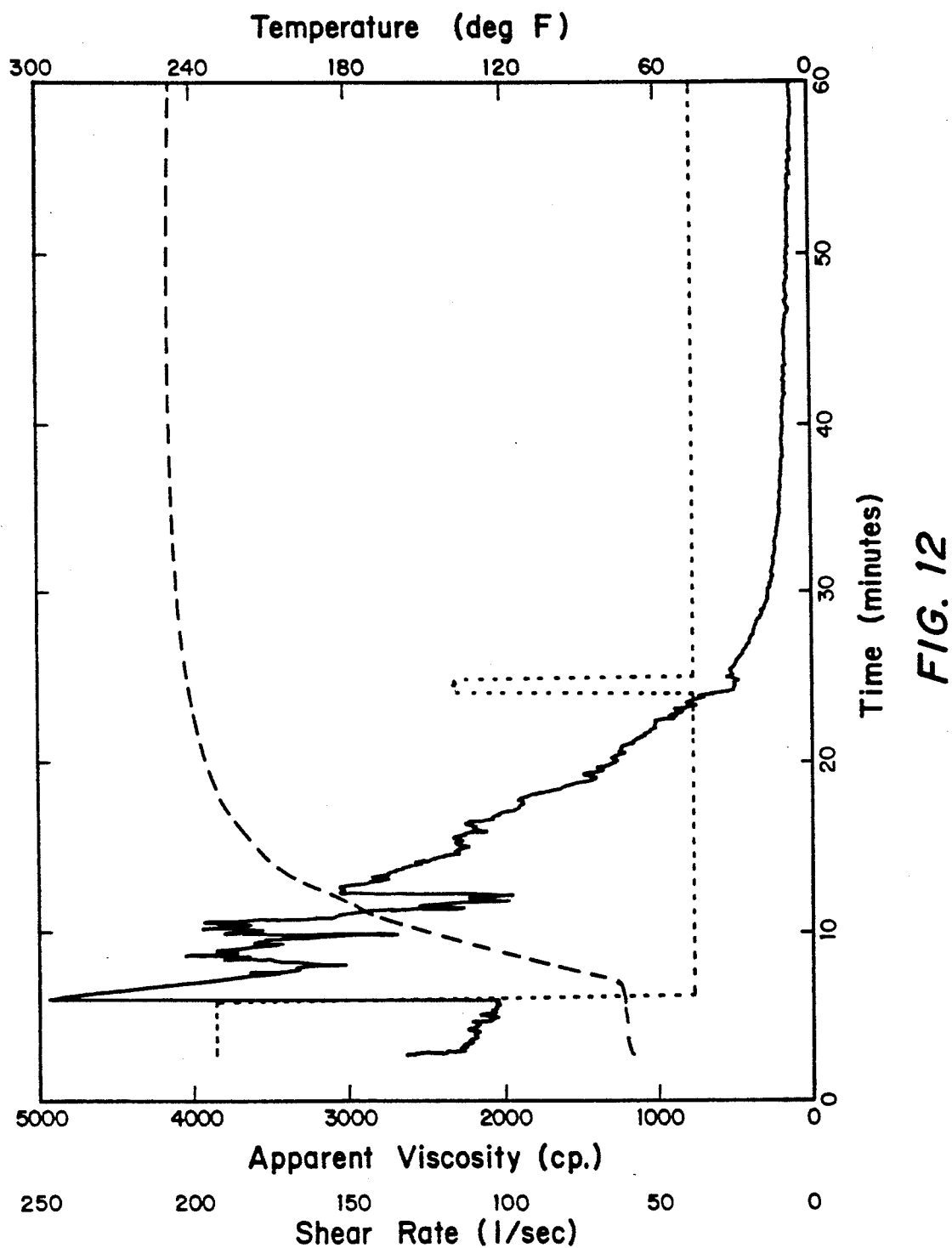
Figure 13:
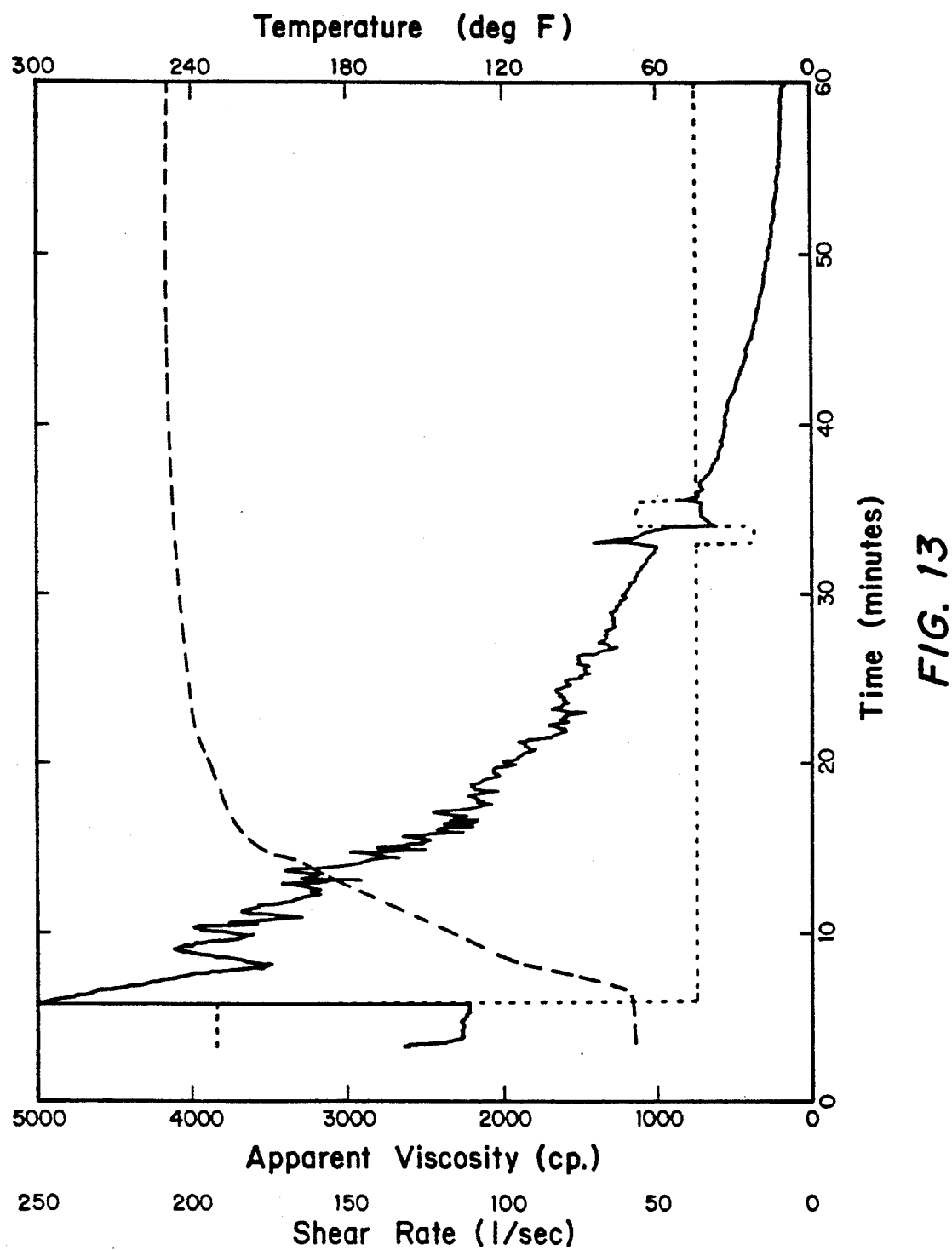
FIGS. 13 and 14 represent graphs of the shear rate and viscosity against time and temperature of the standard boric acid crosslinkers used by industry.
Figure 14:
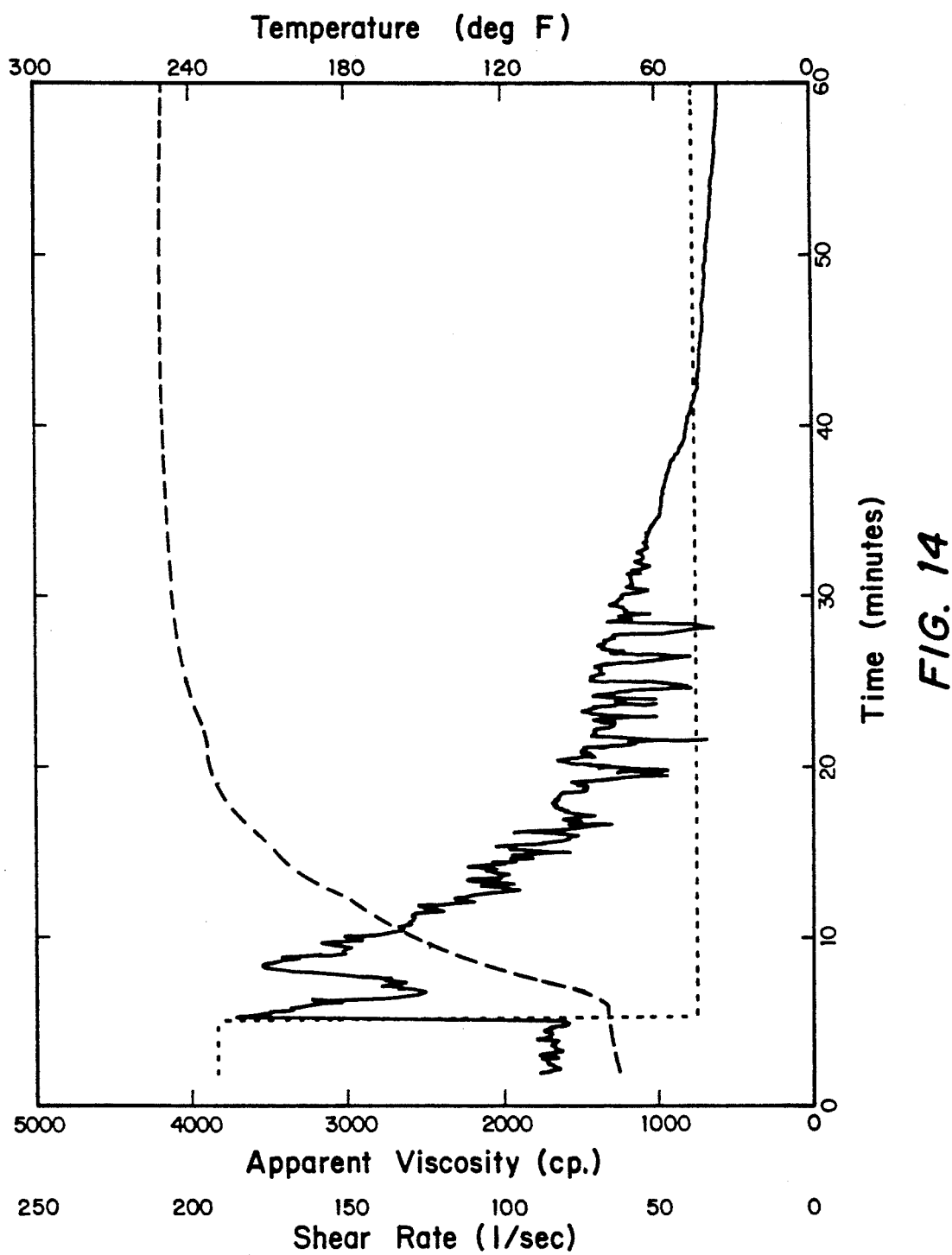

| TEST NO. | EXAMPLE NO. | B₂O₃:ZrO₂ WT. RATIO | SOLUTION/ HPG GPT | BUFFER TYPE | N' | K' | REMARKS OF TEST CONSULTANTS |
| --- | --- | --- | --- | --- | --- | --- | --- |
| 7 | 1 | 10:1 | 2.0 | Soda Ash | .899 | .023 | are no borates that can perform in this manner. The results in FIG. 7 indicate the viscosity was sustained very close to 1000 cp for over 45 minutes and after shear ramping had returned to a viscosity of close to 1000 cp. There was some slip phenomena going on when determining the n' and k'. The novel crosslinker was more efficient at higher temperature (250° F.) than any other known borate crosslinkers in the oilwell industry. |
| 8 | 1 | 10:1 | | Sodium Hydroxide | | | FIG. 8 indicates performance is not as good as Tests 3 and 4, the viscosity was sustained about 1000 cp which is quite good. |
| 9 | 6 | 5:1 | 1.5 | Soda Ash | .4170 | .1966 | Although the viscosity performance in FIG. 9 is acceptable, it does not compare to the BXL-7 at 1¼ gallons per 1000 gallons. Again we do see some slip indicating some need for optimization of buffers and crosslinkers. The performance of this particular fluid is good. |
| 10 | 6 | 5:1 | 2.0 | Soda Ash | .4562 | .2446 | In FIG. 10 this test shows very little difference from FIG. 9. Again slip in the testing indicates the need for optimization of pH buffers and crosslinkers. |
| 11 | 6 | 5:1 | 2.0 | Sodium Hydroxide | | | In FIG. 11, the performance of the caustic soda compared poorly to the performance of soda ash as a buffer system. |
| 12 | 7 | 20:1 | 1.5 | Soda Ash | | | In FIG. 12, this test indicated high initial viscosities and fairly rapid degradation of the fluid. When taken off the Fann, it indicated that it was broken down completely. |
| 13 | 7 | 20:1 | 2.0 | Soda Ash | | | FIG. 13, this test indicated some very high initial viscosities and an improvement over the FIG. 12 test, but when the test was taken off, it indicated a complete breakdown of the crosslink system. |
| 14 | 7 | 20:1 | 2.0 | Sodium Hydroxide | | | The test in FIG. 14 again showed very little difference between the soda ash test with fairly rapid decrease in viscosity. |

Notes:
1. The initial HPG gel viscosities were between 35 and 37, temperatures were between 68° and 76° F., and pHs were between 9.0 and 10.0 for all tests.
2. Soda Ash buffer was 5 ppt and Sodium Hydroxide (NaOH) buffer was 1.2 gpt.
3. Test 1 and 2 are the standard boric acid solutions used by industry.

I claim:

1. A method of preparing stable solutions of boron zirconium chelate comprising:
   a. Preparing a mixture of:
      i. an alpha hydroxy carboxylate selected from the group consisting of ammonia zirconium, water soluble amines zirconium and alkali metals zirconium alpha hydroxy carboxylates;
      ii. a polyol selected from the group consisting of glycerin, erythritol, arabitol, xylitol, sorbitol, dulcitol, mannitol, inositol, monosaccharides and disaccharides; and
      iii. water;
   Said mixture containing sufficient quantities to yield 0.1-3.0% by weight $ZrO_2$ and 5.0-25.0% by weight of at least one of said polyols in the final stable solution of boron zirconium chelate;
   b. Stirring the mixture to achieve uniformity thereof;
   c. Thereafter, adding at least one of boric acid and borax as a source of boron to said mixture while stirring sufficient to yield 2-20% by weight $B_2O_3$ in the final stable solution of boron zirconium chelate while maintaining the weight ratio of $B_2O_3:ZrO_2$ between 5:1 and 20:1;
   d. Then adding sufficient base selected from the group consisting of inorganic and organic bases and inorganic carbonates and bicarbonates to establish the pH of the final stable solution of boron zirconium chelate between 7.0 and 10.0.

2. The method of claim 1 wherein said alpha hydroxy carboxylate is an alkali metal selected from the group consisting of sodium zirconium lactate, citrate, tartrate, glycolate, maleate, saccharate, gluconate, glycerate, and mandelate.

3. The method of claim 1 wherein said alpha hydroxy carboxylate is selected from the group consisting of ammonium zirconium lactate, citrate, tartrate, glycolate, maleate, saccharate, gluconate, glycerate, and mandelate.

4. The method of claim 1 wherein said alpha hydroxy carboxylate is selected from the group consisting of potassium zirconium lactate, citrate, tartrate, glycolate, maleate, saccharate, gluconate, glycerate, and mandelate.

5. The method of claim 1 wherein said alpha hydroxy carboxylate is selected from the group consisting of water soluble amines zirconium lactate, citrate, tartrate, glycolate, maleate, saccharate, gluconate, glycerate, and mandelate.

6. The method of claim 2 wherein said polyol is glycerin and boric acid is added as a source of boron.

7. The method of claim 2 wherein said polyol is glycerin and borax is added as a source of boron.

8. The method of claim 1 wherein at least two polyols are mixed with the said alpha hydroxy carboxylate and boric acid and borax are added as a source of boron and said base is ammonium hydroxide.

9. The method of claim 2 wherein said alkali metal zirconium alpha hydroxy carboxylate is sodium zirconium lactate, the said polyol is sorbitol and the base is sodium hydroxide.

10. The method of claim 3 wherein the said alpha hydroxy carboxylate is ammonium zirconium lactate, the said polyol is glycerin and the said base is ammonium hydroxide.

11. The method of claim 2 wherein said alkali metal alpha hydroxy carboxylate is sodium zirconium citrate, the said polyol is glycerin and the said base is sodium hydroxide.

12. The method of claim 2 wherein said base is an inorganic base selected from the group of sodium hydroxide and potassium hydroxide.

13. The method of claim 1 wherein said inorganic and organic bases and inorganic carbonates and bicarbonates are at least one of triethanolamines, diethanolamines, sodium hydroxide, potassium hydroxide, calcium hydroxide, magnesium hydroxide, sodium carbonate, potassium carbonate, ammonium carbonate, sodium bicarbonate, potassium bicarbonate and ammonium bicarbonate.

14. The method of claim 5 wherein said base is selected from the group consisting of triethanolamines and diethanolamines.

15. The method of claim 5 wherein said base is selected from the group consisting of water soluble organic amines, ammonium carbonate and ammonium bicarbonate.

16. A method of preparing stable solutions of boron zirconium chelate comprising:
   Preparing a mixture of an alkali metal zirconium alpha hydroxy carboxylate; a polyol selected from the group consisting of glycerin, erythritol, arabitol, xylitol, sorbitol, dulcitol, mannitol, inositol, monosaccharides and disaccharides; and water, sufficient to yield 5–25% by weight of at least one of said polyols in the final stable solution of boron zirconium chelate;
   Stirring the mixture to achieve uniformity thereof;
   Thereafter, adding one of boric acid or borax as a source of boron to said mixture while stirring sufficient to yield 2–20% by weight $B_2O_3$ in the final stable solution of boron zirconium chelate while maintaining the weight ratio of $B_2O_3:ZrO_2$ between 5:1 and 20:1;
   Then adding sufficient base selected from the group consisting of inorganic and organic bases to establish the pH of the stable solution of boron zirconium chelate between 7.0 and 10.0.

17. The method of claim 16 wherein the weight ratio of $B_2O_3:ZrO_2$ is between 5:1 and 10:1.

18. The method of claim 16 wherein the weight ratio of $B_2O_3:ZrO_2$ is between 5:1 and 15:1.

19. The method of claim 16 wherein the alkali metal zirconium alpha hydroxy carboxylate is sodium zirconium alpha hydroxy carboxylate.

20. The method of claim 16 wherein the alkali metal zirconium alpha hydroxy carboxylate is potassium zirconium alpha hydroxy carboxylate.

21. The method of claim 19 wherein the base is sodium hydroxide.

22. The method of claim 20 wherein the base is potassium hydroxide.

23. A method of preparing stable solutions of boron zirconium chelate comprising:
   Preparing a mixture of a zirconium alpha hydroxy carboxylate selected from the group consisting of ammonium and water soluble amines zirconium alpha hydroxy carboxylates, a polyol selected from the group consisting of glycerin, erythritol, arabitol, xylitol, sorbitol, dulcitol, mannitol, inositol, monosaccharides and disaccharides, and water, sufficient to yield 5–25% by weight of at least one of said polyols in the final stable solution of boron zirconium chelate;
   Stirring the mixture to achieve uniformity thereof;
   Thereafter, adding one of boric acid or borax as a source of boron to said mixture while stirring sufficient to yield 2–20% by weight $B_2O_3$ in the final stable solution of boron zirconium chelate while maintaining the weight ratio of $B_2O_3:ZrO_2$ between 5:1 and 20:1;
   And thereafter adding a base selected from the group consisting of organic bases, inorganic carbonates and bicarbonates to establish the pH of the final stable solution of boron zirconium chelate between 7.0 and 10.0.

24. The method of claim 23 wherein said zirconium alpha hydroxy carboxylate is ammonium zirconium alpha hydroxy carboxylate and wherein said organic base is ammonium hydroxide.

25. The method of claim 23 wherein said organic bases are one of triethanolamines and diethanolamines.

26. A composition made in accordance with the method of claim 1.

27. A composition made in accordance with the method of claim 16.

28. A composition made in accordance with the method of claim 23.

* * * * *